United States Patent
Kukuk et al.

(10) Patent No.: US 8,233,962 B2
(45) Date of Patent: Jul. 31, 2012

(54) ROTATIONAL STEREO ROADMAPPING

(75) Inventors: Markus Kukuk, Palo Alto, CA (US); Sandy Napel, Menlo Park, CA (US)

(73) Assignees: Siemens Medical Solutions USA, Inc., Malvern, PA (US); The Board of Trustees of the Leland Stanford Junior University, Stanford, CA (US)

( * ) Notice: Subject to any disclaimer, the term of this patent is extended or adjusted under 35 U.S.C. 154(b) by 1808 days.

(21) Appl. No.: 11/434,692

(22) Filed: May 16, 2006

(65) Prior Publication Data

US 2008/0009715 A1    Jan. 10, 2008

(51) Int. Cl.
*A61B 5/05* (2006.01)
*A61B 6/00* (2006.01)
*G01N 23/04* (2006.01)

(52) U.S. Cl. ........ 600/424; 600/431; 600/425; 600/427; 378/62

(58) Field of Classification Search .................. 600/427, 600/431, 425, 424; 378/63, 62
See application file for complete search history.

(56) References Cited

U.S. PATENT DOCUMENTS

| | | | |
|---|---|---|---|
| 4,838,265 A | | 6/1989 | Cosman et al. |
| 5,683,819 A | * | 11/1997 | Mori et al. ............... 428/500 |
| 5,951,475 A | * | 9/1999 | Gueziec et al. ............ 600/425 |
| 6,272,370 B1 | | 8/2001 | Gillies et al. |
| 6,298,259 B1 | | 10/2001 | Kucharczyk et al. |
| 6,351,513 B1 | | 2/2002 | Bani-Hashemi et al. |
| 6,370,417 B1 | | 4/2002 | Horbaschek et al. |
| 6,370,421 B1 | | 4/2002 | Williams et al. |
| 6,389,104 B1 | | 5/2002 | Bani-Hashemi et al. |
| 6,470,207 B1 | * | 10/2002 | Simon et al. ............... 600/426 |
| 6,484,049 B1 | * | 11/2002 | Seeley et al. ............... 600/426 |
| 6,577,889 B2 | * | 6/2003 | Ichihashi ................... 600/425 |
| 6,606,513 B2 | | 8/2003 | Lardo et al. |
| 6,628,977 B2 | | 9/2003 | Graumann et al. |
| 6,725,080 B2 | | 4/2004 | Melkent et al. |
| 6,813,512 B2 | | 11/2004 | Aldefeld et al. |
| 6,923,768 B2 | | 8/2005 | Camus et al. |
| 6,937,883 B2 | | 8/2005 | Prince |
| 2002/0085681 A1 | | 7/2002 | Jensen |
| 2003/0128801 A1 | | 7/2003 | Eisenberg et al. |
| 2003/0181809 A1 | | 9/2003 | Hall et al. |
| 2004/0077942 A1 | | 4/2004 | Hall et al. |
| 2005/0020914 A1 | | 1/2005 | Amundson et al. |
| 2005/0053192 A1 | | 3/2005 | Sukovic et al. |
| 2005/0065430 A1 | | 3/2005 | Wiethoff et al. |
| 2005/0096543 A1 | | 5/2005 | Jackson et al. |
| 2005/0137661 A1 | | 6/2005 | Sra |
| 2005/0143777 A1 | | 6/2005 | Sra |
| 2005/0165301 A1 | | 7/2005 | Smith et al. |
| 2005/0288578 A1 | | 12/2005 | Durlak |
| 2007/0276216 A1 | * | 11/2007 | Beyar et al. ............... 600/407 |

* cited by examiner

*Primary Examiner* — Brian Casler
*Assistant Examiner* — Helene Bor
(74) *Attorney, Agent, or Firm* — Alexander J Burke

(57) ABSTRACT

An improved method is disclosed for imaging in an interventional medical procedure that is more advanced than a conventional 2D image processing application and less restrictive than a 3D reconstruction image processing application. In contrast to the prior art 2D imaging application in which a single 2D image is acquired, the inventive method acquires and stores a set of 2D anatomical images while rotating a C-arm/X-ray source using a single injection of contrast agent. In lieu of performing a 3D reconstruction, the multiplicity of anatomical views provided by the set of 2D anatomical images adequately serve as a visual "rotatable roadmap" to perform classical 2D-roadmapping navigation. The "rotatable roadmap" assists a user to locate an ideal working view of the patient's region of operative interest.

19 Claims, 3 Drawing Sheets

ROTATIONAL STEREO ROADMAPPING

FIELD OF THE INVENTION

The present invention relates generally to medical intervention procedures and more particularly to an improved method for imaging in a medical interventional procedure.

BACKGROUND OF THE INVENTION

The technique known as road-mapping is used in the selective catheterization of vessels in the framework of an interventional treatment. In these minimally invasive, angiographic interventions, an image of a patient's vasculature is obtained for use as a "road map," to assist a physician to efficiently guide or navigate instruments such as catheters or guide-wires through the patient's vasculature. Intravascular procedures are typically performed using a C-arm x-ray imaging system which includes an adjustable x-ray source and an x-ray detector.

Image based navigation using the road-mapping technique can be characterized by the three types of images involved: vessel images (road map of patient's vasculature), fluoroscopy images and navigation images. The vessel image is acquired by injecting a quantity of contrast agent (typically iodine) into the blood stream during x-ray acquisition to visualize the patient's vasculature. This image is retained as a "road map" image. Fluoroscopy images are acquired without the injection of a contrast agent and typically depict dense structures such as bones and instruments. The navigation image is then computed by combining the vessel image with the fluoroscopy image to visualize the live instruments in the context of the vasculature. Presently, the road mapping technique finds application in the prior art in both 2D and 3D image based navigation techniques, both of which are briefly described as follows.

In a 2D image processing application, a series of vessel images is acquired by injecting a relatively small quantity of contrast agent (typically iodine) into the blood to opacify the vessel tree during image acquisition. The C-arm is kept stationary during the acquisition. One vessel image is selected to serve as a so-called "road map". The navigation images are created by combining the single road map image with each live fluoroscopy image for guiding instrumentation (e.g., guide wires, catheters) throughout the vasculature, in real-time.

One drawback associated with the prior art 2D image processing application is that re-positioning of the C-arm to resolve ambiguous plane turns of vessels is done "blindly" on a trial-and-error basis. In other words, a physician or operator makes an educated guess as to how to re-position the C-arm to resolve ambiguity through plane turns of the vessels. Due to the uncertainty of the trial-and-error approach, each trial may have intended or unintended results for navigating through the vasculature. Each trial requires the injection of contrast media at each step. This is highly undesirable from the patient's perspective in that multiple injections of contrast media may or may not be well tolerated in the patient. A further disadvantage of the prior art 2D image processing application is that the single "road map" image obtained at the outset of the procedure is a plain-projection image devoid of depth information.

In a 3D image processing application, a quantity of contrast agent is injected to opacify the vessels. A C-arm is then rotated on a circular trajectory around the patient during the injection. In this manner, a series of high-quality images are acquired, each depicting the vasculature from a different angle. In a subsequent processing step, all acquired images are sent to a reconstruction unit, where a 3D image (volume) of the vessel tree is computed. This 3D image is retained and serves as the vessel image of the 3D road-mapping technique. A 2D vessel image showing the vasculature from any angle can be obtained by re-projecting the 3D vessel image. Similar to the 2D road-mapping technique, this 2D vessel image is combined with a fluoroscopy image to obtain the navigation image. A drawback of the 3D image processing application is that the 3D image of the vasculature has to be acquired such that the result is clinically useful, e.g. depict the vessel tree in pristine quality. In order for the 3D image to be clinically useful, several prerequisites have to be fulfilled. First, the C-arm apparatus must be rotated over an angular range of 180 degrees, at a minimum, to obtain a clinically useful reconstruction of the vessel tree. This necessitates a relatively long processing time (e.g., on the order of 7 seconds) during which a significant amount of contrast agent is injected into the patient. Second, the quality of the 3D reconstruction is proportional to the number of images acquired during the rotational run. In other words, for the highest quality 3D reconstruction, a significant amount of projections have to be acquired, which results in increased radiation exposure to the patient. Third, the time it takes to compute a 3D reconstruction of the vessel tree is proportional to the number of 2D projections input to the reconstruction unit. For a high quality reconstruction, computation time can amount to a significant number. Fourth, there should be as little as possible motion of the anatomy during image acquisition. Too much motion will result in a 3D reconstruction of poor quality. Fifth, there should be no metallic objects, such as stents or coils in the field of view. These objects typically cause streak artifacts in the 3D reconstruction which may diminish image quality.

It would therefore be desirable to develop an improved computer-implemented method of image based navigation for use during an interventional medical procedure that is more advanced than the prior art 2D imaging method, discussed above, and provides guidance in situations where one or more of the above prerequisites of the prior art 3D method, discussed above, are not fulfilled.

SUMMARY OF THE INVENTION

The present invention provides an improved computer-implemented method for imaging in an interventional medical procedure that is more advanced than the prior art 2D image processing application, described above, and less restrictive than the 3D reconstruction image processing application, described above. In contrast to the prior art 2D imaging application in which a single 2D image is acquired, the computer-implemented method of the invention acquires and stores a set of 2D anatomical images while rotating a C-arm/X-ray source using only a single injection of contrast agent. By rotating the C-arm/X-ray source during contrast injection the set of acquired 2D anatomical images advantageously show a portion of the patient's anatomy from multiple views. By providing a multiplicity of views via the pre-stored set of 2D anatomical images, the need to perform a 3D reconstruction is precluded. That is, the 2D images are clinically useful in and of themselves for the purpose of navigating a catheter or guide wire towards a target location. Obtaining a 3D reconstruction of a clinically acceptable image quality imposes a number of restrictions on the acquisition protocol, such as a minimum number of images (e.g. 200) acquired over a minimum angular range (e.g. 180°). These restrictions greatly limit the range of application of all 3D navigation techniques. The inventive computer-implemented method on the other hand provides great flexibility in image acquisition. For example, short scans can be acquired (e.g. 45 images over 90°), which reduces the amount of iodine injected into the patient and minimizes the patient's radiation exposure.

The multiplicity of views provided by the set of 2D anatomical images serve as a visual "rotatable roadmap" for performing classical 2D-roadmapping navigation. In the context of a vasculature procedure, the set of images provides a interventionalist with a multiplicity of views from which to identify and select an ideal working view for each segment of a patient's vessel tree. The ability to identify an ideal working view at each stage of the procedure by selecting a single image for use as an interventional "road-map", renders the injection of additional contrast media unnecessary while minimizing radiation exposure and procedure time.

According to one aspect, a method for imaging in an interventional medical procedure comprises: reviewing a plurality of previously acquired anatomical images of a region of interest in a patient's body to identify an optimal image, selecting said optimal anatomical image based on said review, moving a radiation source and detector to the position at which the selected optimal anatomical image was acquired, constructing a composite image comprised of the selected optimal anatomical image and a live image of said region of interest of said patient, wherein said live image displays a medical device in real-time to be navigated throughout said region of interest in said patient and wherein said composite image displays a relative position and orientation of said medical device to said region of interest, and navigating the medical device an incremental amount towards a target location in said patient in reliance on said composite image.

BRIEF DESCRIPTION OF THE DRAWINGS

A wide array of potential embodiments can be better understood through the following detailed description and the accompanying drawings in which.

DETAILED DESCRIPTION OF EXEMPLARY EMBODIMENTS

The method is applicable to a wide variety of applications. For example, one particularly suitable application is an application in which a conventional 3D reconstruction may not produce a clinically useful image quality. Examples of clinical situations in which a 3D technique may suffer from poor image quality include the presence of motion (e.g., cardiac motion, respiratory motion, patient motion) and the presence of metallic objects, such as stens or coils. In contrast, the inventive method provides high quality vessel images under all of the afore-mentioned conditions.

It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

Figure 1:
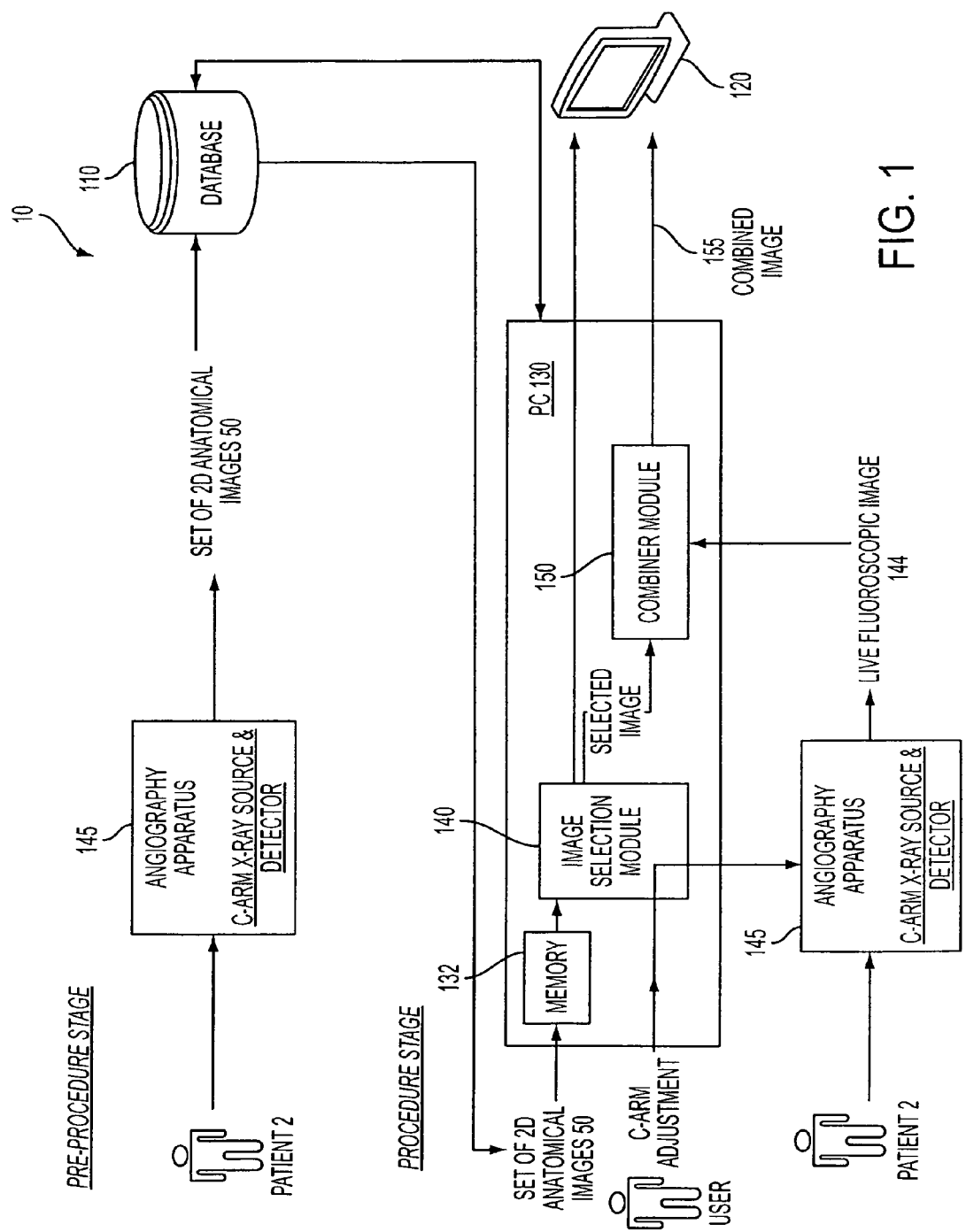
FIG. 1 is an illustrative example of a clinical environment for performing an interventional medical procedure according to an embodiment of the present invention.

Referring now to the figures, FIG. 1A illustrates an example of a clinical environment for performing an embodiment of the present invention. In the clinical environment illustrated in FIG. 1A, a patient 2 is connected to an angiography apparatus 145 during a pre-procedure stage to generate a set of 2D anatomical images 50 of a region of interest of the patient 2 (e.g., the patient's vasculature). The angiography apparatus 145 comprises a C-arm/X-ray source and detector. The set of 2D anatomical images are stored in a data repository 110 coupled to a personal computer (PC) 130 for later recall during a procedure stage.

At the beginning of the procedure stage, the set of 2D anatomical images 50 are recalled from the data repository 110 and stored in a memory 140 of a processor 130. At each stage of the procedure, a single image is selected as being a "best anatomical view" at that stage, to be combined with a live fluoroscopic image 144 to generate a combined image 155 to assist an interventionist in performing the procedure. The images may be displayed on display device 120. The pre-procedure and procedure stages are described in greater detail as follows.

Figure 2:
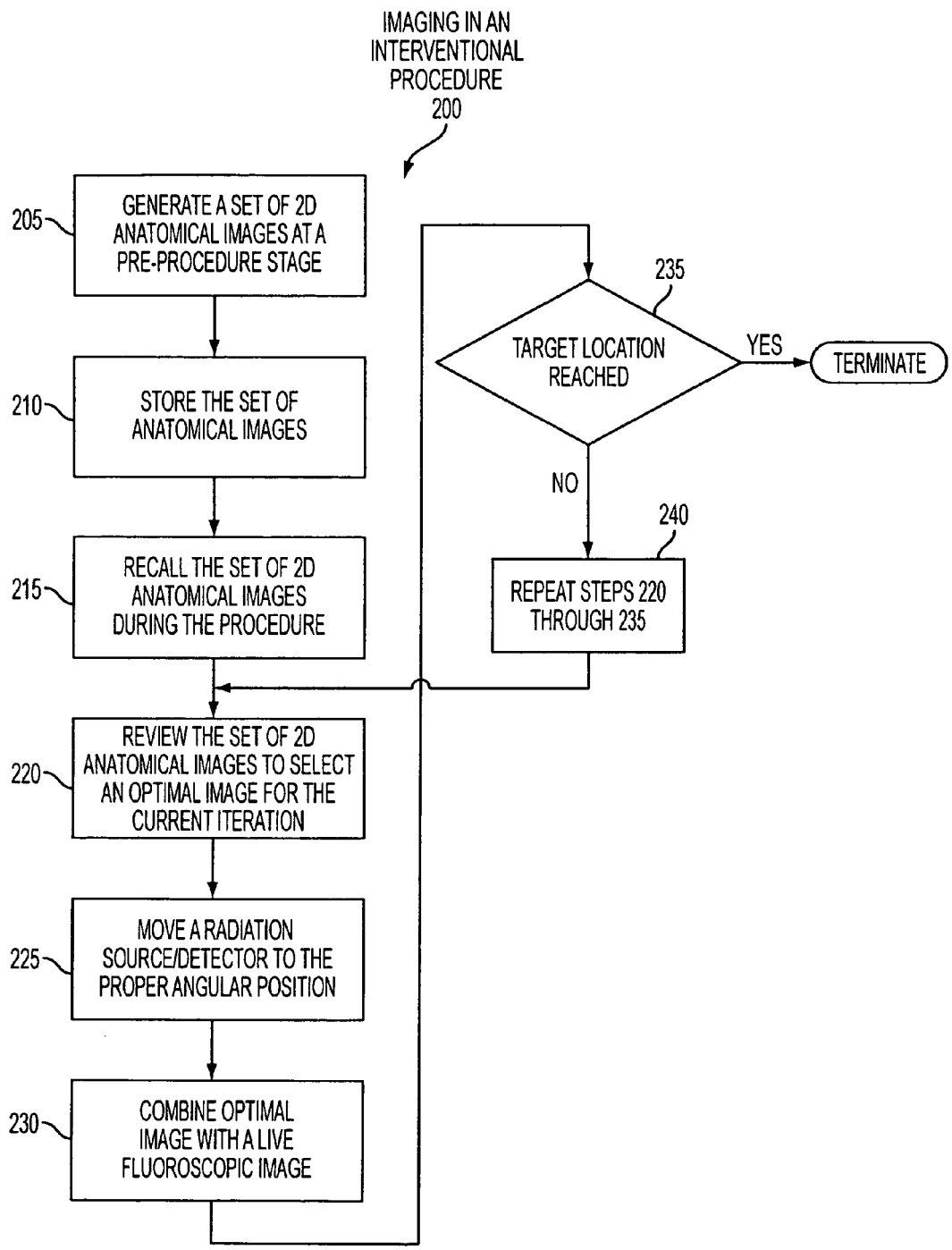
FIG. 2 is a flow chart of a method for imaging in an interventional medical procedure according to an embodiment of the present invention.

FIG. 2 illustrates an exemplary flow diagram (generally designated 200) delineating a method for imaging in an interventional medical procedure, according to one embodiment. Flow diagram 200 illustrates an exemplary sequence of steps for utilizing a set of 2D anatomical images 50 for assisting personnel in performing an interventional medical procedure.

Initially, at step 205, at a pre-procedure stage, a single conventional rotational angiographic acquisition is performed of a particular body region of a patient to generate a set of 2D anatomical images 50 (see FIG. 1), referred to as a "rotational roadmap". In the presently described exemplary embodiment, the single conventional rotational angiographic acquisition utilizes a C-arm x-ray source and detector which is rotated through a pre-determined angular range (e.g., 0-90 degrees) to obtain a set of 2D anatomical images 50 of a region of the patient's anatomy, wherein each of the acquired images in the set of images is obtained at a unique angular position. The images may be evenly spaced, i.e., taken at every 10 degrees, resulting in a set of 10 images.

At step 210, the acquired set of 2D anatomical images 50 are stored in a data repository 110 for later recall by an operator for use during the interventional procedure, as will be described further below. In addition to obtaining the set of images, the angular positions at which each respective image in the set of images is acquired is recorded and stored in the data repository 110.

At step 215, at the start of the interventional procedure, using a conventional display device and associated Graphical User Interface (GUI), the previously stored set of 2D anatomical images of the patient's anatomy are recalled to assist an operator in performing the interventional medical procedure.

At step 220, the operator reviews the set of recalled 2D anatomical images 50, recalled from the data repository 110, to select a single image from among the set of images as a "best anatomical working view", referred to hereafter as an "optimal image", for the particular iteration of the procedure. It is noted that at any particular iteration of the procedure, the operator has the ability to change one or more parameters (e.g. zoom format, source-detector distance, pan) of the angiography apparatus 145 (i.e., the C-arm X-ray Source and detector) to alter the size or position of an acquired live fluoroscopic image 144. The same transformation(s) are applied to the set of recalled 2D anatomical images. For example, if the set of recalled 2D anatomical images 50 were acquired at a zoom format of zero (0) and the operator elects to change the zoom parameter to a zoom format of one (1), the image selection software module 144, running on the PC 130 applies a transformation to the recalled 2D anatomical images 50, such that the recalled 2D anatomical images 50 appear as if they were acquired at a zoom format of one (1). In this way, the recalled 2D anatomical images 50 are always depicted at a zoom format that matches the zoom format of the live fluoroscopic image 144 obtained at that point in the procedure.

At step 225, the C-arm/X-ray source and detector of the angiography apparatus 145 is moved to the previously stored angular position recalled from the data repository. Recall that the angular position is the position at which the selected "optimal image" was acquired during the pre-procedure stage (see step 205).

At step 230, using conventional fluoroscopy techniques, the "optimal image" is combined with the live fluoroscopic image 144 by a combiner module 150 to assist an interventionist in guiding or navigating the medical device an incremental distance towards a target location in the patient 2. The combined image 155 (i.e., optimal image/fluoroscopic image) provides the interventionalist with an image of the medical device's position and orientation relative to the region of interest in the patient's body. For example, in one application, the combined image 155 may show a catheter (as the fluoroscopic component) overlayed over the "optimal image" (as a vasculature component) which assists the interventionalist in visualizing how the catheter needs to be moved with respect to the patient's vasculature. It is noted that the combined image 150 is created from a single fluoroscopic image 144 and a single pre-stored (e.g., vessel) image, selected as an "optimal" image for that particular iteration of the procedure. As is well known in the art, composite images can be constructed in a number of different ways. One way is to subtract a first image from a second image. Another well-known technique is to blend two images whereby X % of a fluoroscopic image is added to a complimentary amount (i.e., 100-X %) of the selected pre-stored image (optimal image). It is further noted that according to accepted convention in the medical imaging arts, it may be preferable to invert the "optimal" image such that dark structure becomes light and the light structure become dark. This may be desirable, for example, in a vascaluture application, whereby blood-vessels become light after inversion and therefore provide good contrast with respect to instruments such as guide-wires or catheters, which are typically depicted as dark structures. It is noted that the afore-mentioned examples are provided by way of illustration and not limitation.

Step 235 is a determination step at which it is determined if the target location is reached. If the target location has been reached at this point, the procedure is terminated. Otherwise, if the target location has not yet been reached, the procedure continues at step 240. It is noted that in certain interventional medical procedures, multiple target locations may be involved. In a multiple target procedure, upon reaching a first target location, navigation proceeds towards the next target location in the same manner.

At step 240, steps 220 through 235 are repeated for another iteration of the procedure to further assist an interventionalist in moving a medical device incrementally further towards a target location.

The following example is presented to illustrate the advantages of the invention, according to an exemplary embodiment, and to assist one of ordinary skill in making and using the same. This example is not intended in any way to otherwise limit the scope of the disclosure. In the example, the described method can generally divided into two stages, a pre-procedure stage and a procedure stage.

In the pre-procedure stage, as described in the flowchart of FIG. 2 at step 205, a single conventional rotational angiographic (RA) acquisition is performed over a particular body region of a patient to generate a single set of 2D anatomical images 50 to provide a multiplicity of views of a particular body region. The set of anatomical images is sometimes referred to herein as a "rotational roadmap". Table I illustrates the result of performing an exemplary conventional RA run over an angular distance of 90 degrees while obtaining a single image every 10 degrees. As shown in Table I, the exemplary RA run results in a set of 10 anatomical images of the patient's anatomy which collectively constitute the "rotational roadmap". As will be described in greater detail below, at each iteration of the procedure, the set of 10 anatomical images are referred to by the operator to identify and select an optimal image for navigating a medical device towards a target location in the patient 2.

TABLE I

| C-arm position identifier | C-arm Angle (in degrees) | Acquired Image Identifier (rotational roadmap) |
|---|---|---|
| Position 1 (start) | 0 | Image 1 |
| 2 | 10 | 2 |
| 3 | 20 | 3 |
| 4 | 30 | 4 |
| 5 | 40 | 5 |
| 6 | 50 | 6 |
| 7 | 60 | 7 |
| 8 | 70 | 8 |
| 9 | 80 | 9 |
| Position 10 (finish) | 90 | Image 10 |

Table II illustrates, by way of example, a procedure composed of 5 iterations during which a medical device is incrementally advanced towards a target location at each iteration.

TABLE II

| Iteration | Device movement per iteration | Optimal Image | Acquired at C-arm angle | Target reached |
|---|---|---|---|---|
| 1 | 3 cm. | Image 5 | 40 degrees | No |
| 2 | 2 cm. | Image 4 | 30 degrees | No |
| 3 | 1 cm. | Image 7 | 60 degrees | No |
| 4 | 5 cm. | Image 2 | 10 degrees | No |
| 5 | 4 cm. | Image 3 | 20 degrees | Yes |

At the beginning of the procedure, i.e., the first iteration (see row 1 of Table II), the medical device (e.g., catheter or guide-wire) is positioned by an operator at a starting location in the patient's anatomy. The set of 2D anatomical images 50, acquired during the pre-procedure stage, are recalled from the data repository 110 for display. At the first iteration, the operator reviews one or more of the set of 2D anatomical images 50, as is necessary, to select an optimal image for navigating the medical device an incremental distance forward towards a target location in the patient 2.

In the example, the operator may review one or more of the 10 pre-stored 2D anatomical images 50 and selects the $5^{th}$ image as being an optimal image (i.e., "best anatomical view") for navigating the medical device an incremental amount towards the target location in the patient 2. Upon selecting optimal image 5, the C-arm x-ray source and detector 145 move to an angular position of 40 degrees, corresponding to the $5^{th}$ image's pre-recorded angular position. The $5^{th}$ anatomical pre-stored image is combined with a live fluoroscopic image 144 of the medical device to provide the operator with a visual aid displaying, in real-time, how the medical device is physically positioned and oriented relative to the patient's body.

Generally, it should be understood that for each iteration of the procedure, a combined image is constructed. The combined image is comprised of a single pre-stored 2D anatomical image 50, selected as an optimal image, and a live fluoroscopic image 144.

Subsequent to navigating the medical device at the end of each iteration, a determination is then made regarding whether or not the target location has been reached. If the target location is reached, the procedure terminates. Otherwise, if the target location has not yet been reached, the procedure continues for another iteration. It is noted that in certain interventional medical procedures, multiple target locations may be involved. In a multiple target procedure, upon reaching a first target location, navigation proceeds towards the next target location.

In the example, it is determined that the target is not reached after the first iteration. Consequently, the procedure continues with successive iterations to reach the target location. At the next iteration of the procedure, iteration 2, the operator re-reviews one or more of the pre-stored 2D anatomical images 50 in the context of the new updated position of the medical device to select a new optimal image. In the example, for the second iteration, the operator selects the $4^{th}$ 2D anatomical image as being an "optimal image". Accordingly, the C-arm x-ray source and detector 145 move to an angular position of 30 degrees, corresponding to the $4^{th}$ image's pre-recorded angular position. The selected image, image 4, is combined with a live fluoroscopic image 144 of the medical device to provide a visual representation of how the medical device is presently physically oriented relative to the patient's anatomy. As described above, the operator utilizes the combined image as a visual aid for guiding or navigating the medical device an incremental distance forward. In the current iteration, the device is moved forward 2 cm utilizing in visual reliance on the combined image (i.e., $4^{th}$ pre-stored 2D anatomical image combined with the live fluoroscopic image 144).

This process is repeated in a similar manner to that described above for a number of required iterations until the target location is reached. In the instant example, 5 iterations are required to reach the target location.

In the embodiment described immediately above, at each iteration, the set of pre-stored 2D images 50 are first reviewed (e.g., browsed by the operator), followed by a selection of a single optimal image followed by movement of the C-arm x-ray source and detector assembly 145 into an angular position corresponding to the position at which the selected optimal image was acquired. It is noted that these three steps (i.e., review, select, move) are performed in substantially sequential fashion.

By contrast, in the present embodiment, the afore-mentioned steps (i.e., review, select, move), are performed substantially in parallel. In accordance with the present embodiment, as the C-arm x-ray source and detector assembly 145 is moved back and forth through the acquisition range, a particular one of the set of pre-stored 2D anatomical images 50 that is closest in angular degrees to the current position of the C-arm x-ray source and detector angular position is displayed to the operator.

It should be appreciated that by virtue of linking the C-arm movement to the display of the set of 2D anatomical images 50, the afore-mentioned steps (i.e., review, select, move), are performed substantially in parallel. In other words, as the C-arm x-ray source and detector move, one of the pre-stored images is automatically available for review. The C-arm x-ray source and detector may be stopped at the moment the operator determines that the currently displayed pre-stored 2D image projection is optimal to effect the selection process.

It is contemplated to also show the operator the angular deviation, between the current C-arm position and the C-arm position of the currently displayed pre-stored 2D anatomical image. The angular deviation may be shown numerically, graphically or as a combination of the two. In this manner, the operator is provided with the ability to fine tune the C-arm position until a desired accuracy is achieved. Unlike the previous embodiment in which the C-arm moved to the precise angular position associated with the selected pre-stored image, in the present embodiment, it may be sufficient and/or desirable to position the C-arm a degree or two offset from the pre-stored positions associated with the set of 2D anatomical images. This determination is made by an experienced operator studying the images as they are displayed to him or her in real-time on a display device.

Figure 3:
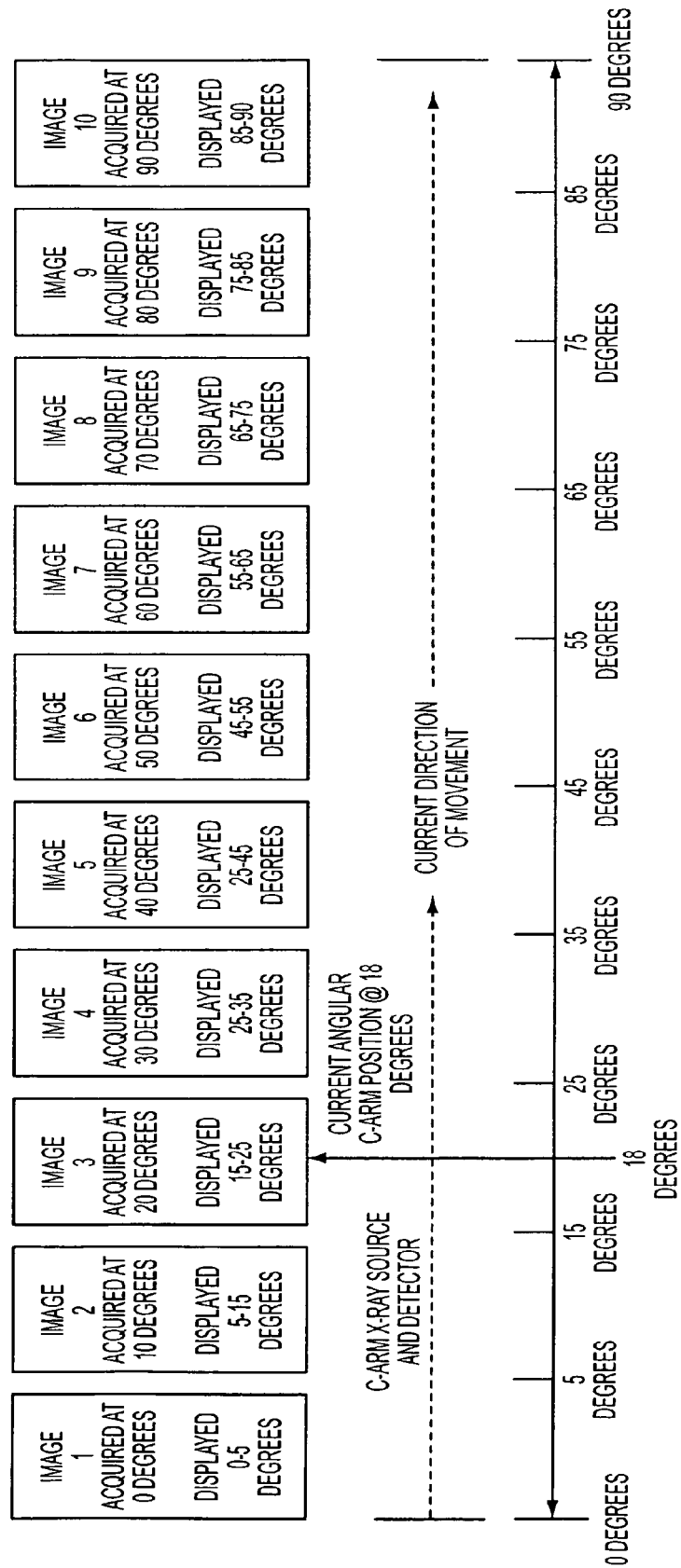
FIG. 3 is a process flow diagram for performing an interventional medical procedure according to an embodiment of the present invention.

With reference now to FIG. 3, a process 300 is shown for performing an interventional medical procedure, according to one embodiment. In accordance with the present exemplary embodiment, an operator controls the movement of the C-arm x-ray source and detector in the acquisition range, for example, 0-90 degrees. As the C-arm x-ray source and detector are moved inside of this range, a single pre-stored anatomical image from the plurality of pre-stored 2D anatomical images, is displayed to the operator at any time on a display device. The image displayed is chosen to be the one whose stored position is closest to the current C-arm position.

FIG. 3 illustrates, by way of example, the method of the second embodiment in which the operations of review, movement and selection are performed substantially in parallel. In accordance with the example, an C-arm x-ray source is presently positioned at 18 degrees. At 18 degrees, the operator is shown pre-stored image 3 as being the closest pre-stored 2D anatomical image to the current angular position of 18 degrees. That is, pre-stored image 3 was previously acquired at 10 degrees, thus the difference between the acquired position and the present position is 8 degrees (18-10). If the operator elects to move the C-arm x-ray source in a "positive" direction (i.e., towards 90 degrees), the operator is shown images 4, 5, 6, . . . 10 in successive order, transitioning from one image to the next as it crosses the successive boundary thresholds shown in FIG. 3. For example, as the C-arm x-ray source transitions from 45 degrees to 46 degrees, image 5 is replaced by image 6 for display. It should be understood that while the instant explanation describes forward movement, the operator controls the back and forth movement of the C-arm x-ray source and detector 145, as is necessary, to analyze the set of acquired images 50 to isolate an optimal image (i.e., best working view) for the particular iteration of the procedure.

In addition to displaying a pre-stored 2D anatomical image 50, the operator may also be shown a numerical and/or visual representation of the deviation (in degrees) between the current position of the C-arm x-ray source and detector and the pre-recorded position of the C-arm x-ray source and detector of the currently displayed image. For example, at the point in time at which the C-arm is at an angular position of 17 degrees, the operator is shown, pre-stored image 3. The operator is also shown a parameter indicating the difference in degrees between the pre-recorded angular position of pre-stored image 3 (20 degrees) and the current angular position of the C-arm device (17 degrees). In this case, the angular difference of deviation is shown to be 3 degrees. Displaying the angular deviation to the operator is advantageous in that it allows the operator to fine tune the position of the C-arm x-ray source and detector to obtain an optimal position for navigating the catheter or guide-wire device an incremental distance through the patient's anatomy towards a target location.

In one embodiment, it is contemplated to acquire a sufficient number of images at successive angular increments that are sufficiently small to display the plurality of anatomical images in stereo to an operator. By way of example, and not limitation, consider a scenario in which a pre-procedure iteration for acquiring the plurality of anatomical images comprises rotating a radiation source and detector over 180 degrees producing 180 projection images. This exemplary pre-procedure operation yields 175 stereoscopic pairs, assuming a 5 degree eye separation, which is conventional. For this particular example, image 1 and 5, image 2 and 6, image 3 and 7 and so on, form a stereo pair. The stereo pairs may be visualized in stereo using well-known stereo visualization techniques. The stereoscopic views show the patient's vasculature (i.e., blood vessels) in stereo, adding depth perception to an otherwise traditionally 2D workflow.

In a single-source C-arm system, the medical device to be navigated through the patient's vasculature can only be shown from one of two viewpoints. However, correction algorithms can be used to estimate the shape of the instrument in one view based on its appearance in a given view. In a multi-source C-arm system such as a bi-plane system or a system featuring x-ray tubes with a movable focal spot, instruments can be directly visualized in stereo.

It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

The present invention provides an improved computer-implemented method for imaging in an interventional medical procedure that is more advanced than a conventional 2D image processing application and less restrictive than a 3D reconstruction image processing application. Specifically, the inventive method overcomes the drawbacks associated with prior art 2D image processing applications which need to constantly re-position the C-arm X-ray source to resolve ambiguous through plane turns of vessels, which is done "blindly" on a trial-and-error basis. The set of 2D images obtained in accordance with the inventive method are recognized as being clinically useful in and of themselves. This is in contrast to 3D image processing applications that require a subsequent 3D reconstruction step for which several prerequisites have to be fulfilled in order to obtain a clinically useful reconstruction of the vessel tree. Namely, the C-arm apparatus must be rotated over an angular range of 180 degrees, at a minimum, necessitating a relatively long processing time during which a significant amount of contrast agent is injected into the patient (injection duration in the order of 6 seconds), the quality of the 3D reconstruction is proportional to the number of images acquired during the rotational run, and the time it takes to compute a 3D reconstruction of the vessel tree is proportional to the number of 2D projections input to the reconstruction unit. Further, the inventive method is applicable to a wide variety of applications, such as applications in which a 3D reconstruction may not produce a clinically useful image quality (e.g., short scans, cardiac motion, respiratory motion, patient motion) and in the presence of metallic objects, such as stens or coils. For example, with the inventive method, the C-arm apparatus may be rotated over an angular range of 72 degrees, which requires a processing time of only 2 seconds and a total injection duration of only 3 seconds. The inventive method provides high quality vessel images and therefore high-quality guidance under all of these conditions.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A computer-implemented method for imaging in an interventional medical procedure using an imaging system including a rotatable arm including a radiation emitting device located towards one end of said rotatable arm and a detector device located towards the opposite end of said rotatable arm, said detector device acquiring radiation emitted by the emitting device and having passed through a patient, the method comprising:
    (a) storing a plurality of 2D anatomical images of a region of interest in a patient's body acquired at different rotatable arm angles and angular data identifying individual respective angles of said rotatable arm at which corresponding 2D anatomical images are acquired;
    (b) receiving user entered data selecting an optimal image from said plurality of 2D anatomical images in response to presenting data to a user identifying to said user said plurality of 2D anatomical images and associated corresponding rotatable arm angles;
    (c) moving a radiation source and detector to a pre-stored angular position associated with said selected optimal image using said angular data;
    (d) constructing a composite image comprised of the selected optimal 2D image and a live 2D image without performing 3D image reconstruction, wherein said live image comprises a medical device displayed in real-time;

(e) displaying said composite image, wherein said composite image comprises data identifying a displayed angular position and orientation of said medical device relative to said selected optimal anatomical image of said region of interest of said patient.

2. The method of claim 1, further comprising acquiring said plurality of 2D anatomical images preoperatively and displaying said plurality of 2D anatomical images and wherein the received data is received in response to user data entry and review of the displayed plurality of 2D anatomical images.

3. The method of claim 2, wherein the step of acquiring said plurality of 2D anatomical images further comprises the steps of:

rotating said radiation source/detector proximate said patient's region of interest;

acquiring each of said plurality of anatomical images at a unique position during said rotation; and recording each of said respective unique positions during said rotation.

4. The method of claim 3, further comprising:

storing each of said acquired plurality of anatomical images; and storing each of said recorded unique positions associated with each of said acquired anatomical images.

5. The method of claim 3, wherein the unique position comprises a unique angular position.

6. The method of claim 2, wherein the step of acquiring said plurality of images occurs while injecting the patient with a single injection of contrast agent.

7. The method of claim 1, further comprising the steps of:

repeating steps (a) through (e) in the case where it is determined that said target location is not reached;

determining if there is at least one additional target location; and repeating steps (a) through (e) in the case where it is determined that there is at least one additional target location; and otherwise terminating said medical procedure.

8. The method of claim 1, wherein said radiation source comprises an x-ray radiation source.

9. The method of claim 1, wherein the received data is automatically provided in response to automatic selection of an optimal image as an image of said plurality of 2D anatomical images acquired at an angle of said rotatable arm closest to a current angular position of said rotatable arm.

10. The method of claim 1, wherein said live image is a live fluoroscopic image.

11. The method of claim 1, further comprising the step of finding a corresponding image to the currently displayed image from said plurality of 2D anatomical images to form a stereo-pair providing a user with depth perception, and wherein said stereo-pair is displayed stereoscopically.

12. A non-transitory computer readable medium having program instructions stored thereto for implementing the method claimed in claim 1 when executed in a digital processing device.

13. A computer-implemented method for imaging in an interventional medical procedure using an imaging system including a rotatable arm including a radiation emitting device located towards one end of said rotatable arm and a detector device located towards the opposite end of said rotatable arm, said detector device acquiring radiation emitted by the emitting device and having passed through a patient, the method comprising:

(a) storing a plurality of 2D anatomical images of a region of interest in a patient's body acquired at different rotatable arm angles and angular data identifying individual respective angles of said rotatable arm at which corresponding 2D anatomical images are acquired;

(b) automatically identifying a particular anatomical image from among said plurality of 2D anatomical images in response to said angular data;

(c) automatically displaying the identified particular anatomical image;

(d) constructing a composite image comprised of the selected optimal 2D image and a live 2D image of a medical device displayed in real-time without performing 3D image reconstruction; and (e) displaying said composite image, wherein said composite image comprises data identifying a displayed angular position and orientation of said medical device relative to said selected optimal anatomical image of said region of interest of said patient.

14. The method of claim 13, further comprising, determining a current position of said radiation source/detector comparing the current position of the radiation source/detector with a pre-stored position of said particular pre-stored image being displayed;

displaying the difference in degrees between the current position of the radiation source/detector and the pre-stored position of said particular pre-stored image being displayed; and adjusting the position of the radiation source/detector until said difference is determined to be less than a pre-determined difference threshold.

15. The method of claim 13, further comprising the step of finding a corresponding image to the currently displayed image to form a stereo-pair providing a user with depth perception, and wherein said stereo-pair is displayed stereoscopically.

16. The method of claim 13, wherein said radiation source comprises an x-ray radiation source and said live image is a live fluoroscopic image.

17. The method of claim 16, wherein said step of automatically identifying a particular anatomical image from among said plurality of 2D anatomical images is performed by automatic selection of an image of said plurality of 2D anatomical images acquired at an angle of said rotatable arm closest to a current angular position of said rotatable arm.

18. The method of claim 17 including the step of automatically identifying a new particular anatomical image from among said plurality of 2D anatomical images by automatic selection of an image of said plurality of 2D anatomical images acquired at an angle of said rotatable arm closest to a current angular position of said rotatable arm as said arm is rotated.

19. A non-transitory computer readable medium having program instructions stored thereto for implementing the method claimed in claim 13 when executed in a digital processing device.

* * * * *